United States Patent [19]
Goodrich, Jr. et al.

[11] Patent Number: 4,973,327
[45] Date of Patent: Nov. 27, 1990

[54] BLOOD BAG FOR LYOPHILIZATION

[75] Inventors: Raymond P. Goodrich, Jr., Pasadena, Calif.; Johannes Derksen, Groningen, Netherlands; Roger W. Hackett, Pasadena, Calif.

[73] Assignee: Cryopharm, Pasadena, Calif.

[21] Appl. No.: 429,948

[22] Filed: Nov. 1, 1989

[51] Int. Cl.5 .............................................. A61B 19/00
[52] U.S. Cl. ..................................... 604/408; 383/119
[58] Field of Search ............... 604/403, 408, 409, 410, 604/415, 416; 383/104, 119

[56] References Cited

U.S. PATENT DOCUMENTS

| 3,319,684 | 5/1967 | Calhoun | 604/408 X |
| 4,443,220 | 4/1984 | Haver et al. | 604/408 |
| 4,622,693 | 11/1986 | Mykleby | 383/119 |
| 4,903,859 | 2/1990 | Derby et al. | 383/119 |

Primary Examiner—Robert A. Hafer
Assistant Examiner—Lynda M. Cofsky
Attorney, Agent, or Firm—Flehr, Hohbach, Test, Albritton & Herbert

[57] ABSTRACT

A lyophilization bag is provided in which a fluid, such as blood, ay be introduced, lyophilized without collapsing the bag, stored, reconstituted and distributed from the bag without intermediate transfer of the useful contents from the bag.

14 Claims, 1 Drawing Sheet

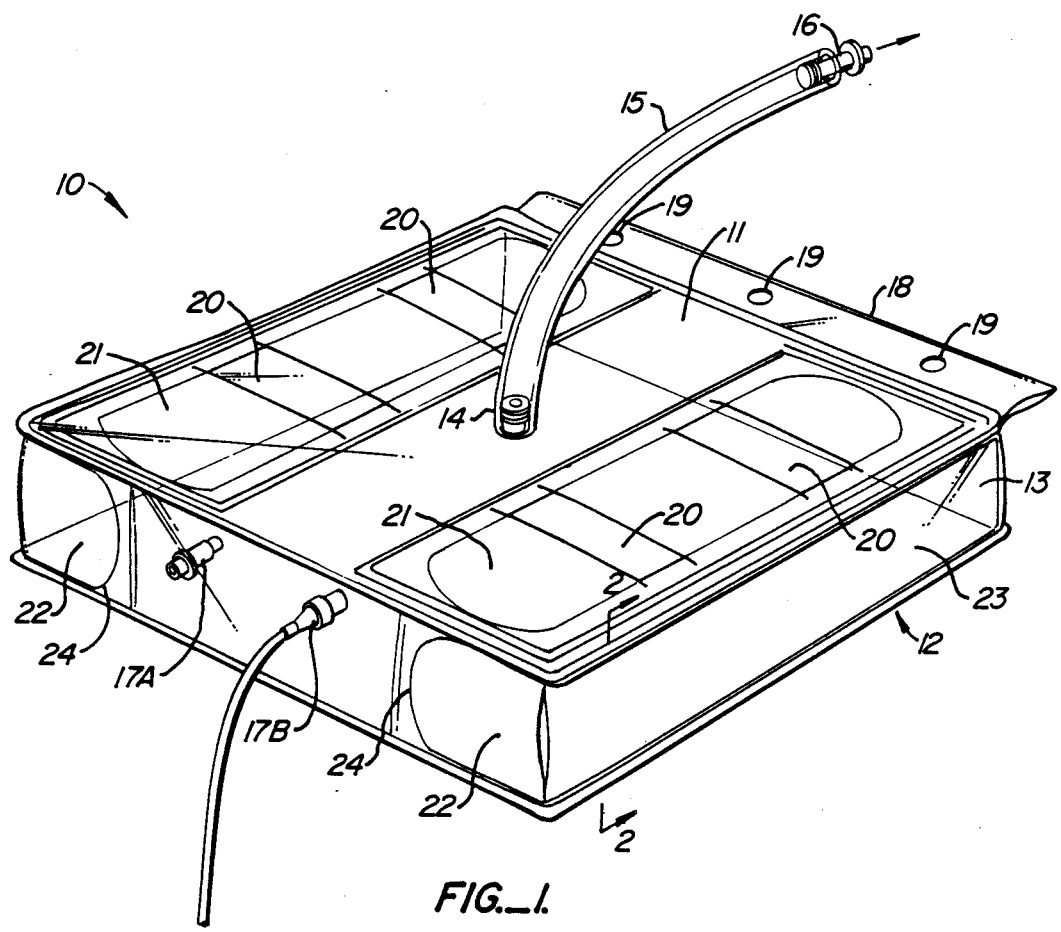
FIG._1.
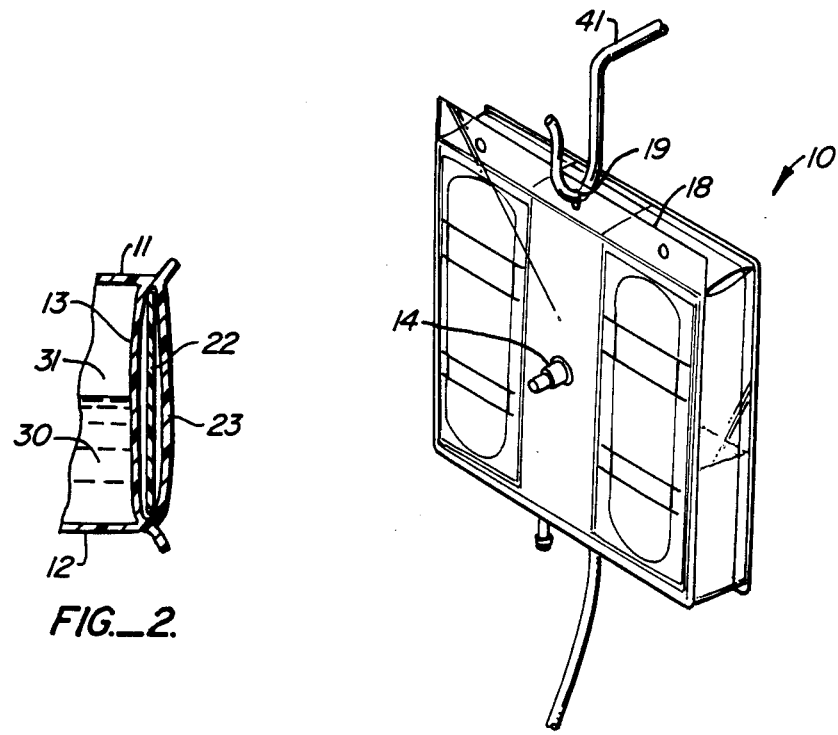
FIG._2.   FIG._3.

BLOOD BAG FOR LYOPHILIZATION

This invention relates to a bag for use in the lyophilization (freeze-drying) of a fluid, particularly blood and red blood cells for transfusion, and which can also be used for storage and reconstitution of the lyophilized product. The blood bag for lyophilization according to this invention can also be used for the lyophilization, storage, and reconstitution of blood substitutes, such as liposome encapsulated hemoglobin (hemosome) solutions and cell-free hemoglobin solutions; fluid blood components, including serum and fractions derived from serum; or any protein-containing solution or suspension.

BACKGROUND OF THE INVENTION

There are several practical problems which are encountered in the lyophilization, storage and reconstitution of fluid products, particularly blood. One of the objects, particularly in dealing with blood or other medical products, is to handle the blood as little as possible to minimize exposure to sources of possible contamination. Furthermore, the blood should be able to be conveniently stored in its lyophilized state in a sterile environment and then reconstituted with as little handling as possible and with minimal exposure to possible sources of contamination.

There is the practical problem of conservation of storage space. It would be desirable to have the container in which the blood is stored take up the minimum amount of room, since in many instances, it is stored in a controlled temperature environment, such as a refrigerator, in which space is limited.

Another problem is that the container for the blood must not only be susceptible to sterilization, but must also mechanically withstand low temperatures, particularly, for example, liquid nitrogen temperatures, used for lyophilization processes, and withstand application of a vacuum.

To minimize storage utilization, the above requirements suggest the use of a flexible, collapsible container. On the other hand, if the contents of the bag are to be lyophilized under vacuum, the bag must be able to withstand application of a vacuum without collapsing during lyophilization.

It is thus an object of the present invention to provide a lyophilization bag which can be used during lyophilization, then collapsed to conserve space during storage, which is versatile enough to allow one to reconstitute the contents within the bag so that they may be used directly from the bag, which will provide a fully-enclosed sterile container system. Thus, according to the invention, the same container may be used for lyophilization, storage and reconstitution, thus avoiding transfers of the contents for these purposes.

This and other objects of the invention will be apparent from the following description and accompanying drawings and appended claims.

SUMMARY OF THE INVENTION

The present invention provides a collapsible, flexible plastic bag comprising an upper wall and a lower wall sealed to a peripheral side wall. The upper wall has a major port adapted with a sealable conduit, and the side wall has at least one side port adapted with sealing means and located approximate to the upper edge of the side wall. The side wall and upper wall are adapted with a securing means to receive removable reinforcing members to restrain the respective walls from flexing and collapsing the bag. The lower wall has a securing means to accommodate a removable lowering reinforcing member, which member is also made of a thermally conducting material to permit cooling of the contents of the bag through the bottom wall. The bag is also adapted with an attachment means for suspending the bag in a position whereby at least one of the side ports is at a location for withdrawing the fluid contents from the bag.

BRIEF DESCRIPTION OF THE DRAWING

FIG. 1 is a perspective view of the preferred embodiment of a lyophilization bag according to the present invention.

FIG. 2 is a partial cross-section view through section line 2—2 of FIG. 1 of a side wall, reinforcing member and a securing flap therefor.

FIG. 3 is a perspective view of the lyophilization bag of FIG. 1 suspended in a position for withdrawing the liquid contents therefrom through one of the side ports.

DESCRIPTION OF THE PREFERRED EMBODIMENTS

Referring to FIG. 1 there is shown a bag 10 made of a flexible plastic material. The preferred material is a polymeric substance comprising polyvinylchloride film plasticized with plasticizer, such as polyvinylchloride Grade 6 (made by Ellay, Inc., Commerce, Calif. As shown, the bag comprises an upper wall 11 and a lower wall 12 which are peripherally bonded to a peripheral wall 13. As shown, the bonded edges between the upper wall 11 and the lower wall 13 and, between the lower wall 12 and peripheral wall 13 may be made by heat or radiofrequency sealing the edges of the walls. However, any equivalent means of sealing the walls together to form the bag may be utilized. The upper wall 11 accommodates a port 14 which, as shown, is approximately centrally located on upper wall 11. To the port 14 is affixed conduit 15, at one end of which is fitted a removable sealing plug 16. In an alternate embodiment the conduit 15 may be omitted and the port 14 may be directly sealed with a removable plug similar to that shown as 16. At one end of the peripheral wall 13 there is shown a plurality of sealable side ports 17A and 17B. These ports are also affixed with plastic adapters such as polyethylene similar to port 14. The side ports 17A and 17B, as shown, are located proximate to the upper edge of the juncture between the peripheral wall 13 and upper wall 11 so as to avoid plugging of these ports by any material within the bag 10 when the bag is partially filled with a liquid or other fluid substance while it rests flat on bottom wall 12 on a level surface.

On the side of the bag 10 opposite to the ports 17A and 17B is located a tab 18 which, as shown, is bonded to the upper edge of upper wall 11. Tab 18 accommodates a plurality of orifices 19 from which the bag 10 can be suspended, as further described hereinbelow in connection with FIG. 3. Since bag 10 is made of a flexible material, the bag would be collapsible, if not reinforced. Accordingly, as shown in FIG. 1, there is shown on upper wall 11 loops which are bonded to the upper wall 11 which retain reinforcing inserts 21. The reinforcing inserts 21 may be made of rigid or semi-rigid material, such as polyethylene, of sufficient strength to prevent collapsing of bag 10, and in particular, to prevent collapsing of upper wall 11 when a vacuum is applied to the interior of bag 10 by withdrawal of gas and other vapors through port 14. The inserts 21 need only be of sufficient strength to prevent the collapse of wall 11 when vacuum pressures normally used in lyophilization processes are applied within the bag 10.

Similarly, to prevent collapse of peripheral wall 13 loops 22 and 23 are affixed to the peripheral wall 13. As shown, a single reinforcing insert 24 is utilized, which is inserted into loops 22 and 23 and corresponding loops (not shown) on the sides of the peripheral wall 13 which cannot be directly viewed in FIG. 1. A single reinforcing insert 24 is appropriately bent to accommodate the corners of the bag when inserted through loops 22 and 23. The reinforcing insert 24 may be made of the same rigid or semi-rigid polyethylene material as inserts 21.

The bottom wall 12 of bag 10 may also be bonded, preferably on three of its edges, to an exterior flap to form a pocket (not shown) to receive a lower reinforcing member (not shown) to support bottom wall 12. Any convenient configuration for supporting a rectangular reinforcing member on the exterior of wall 12 may be utilized. Instead of a semi-rigid plastic insert, however, the reinforcing member for bottom wall 12 is preferably a copper plate of a size approximately coextensive with the wall 12. The copper plate will serve as a thermal conductor when the bag is cooled to conduct heat away from the contents of the bag, which lie along the bottom of the bag 10, to assist in cooling during the initial freezing of the liquid, and then during subsequent lyophilization. After lyophilization the reinforcing copper plate may be removed, so the flexible bag may be more conveniently stored, and also to conserve copper plates and reduce the overall weight of the bag and its dried contents.

The seal to port 17A may be sealed until use. Similarly, port 17B and plug 16 are sealed until use.

Referring to FIG. 2 there is shown a partial cutaway detail of peripheral wall 13, reinforcing insert 24 and retaining loop 23 along line 2—2 of FIG. 1. As shown in FIG. 2, the wall 13 is supported from collapsing by reinforcing insert 24 which is retained in position by loop 23. The bag is not filled to its fullest extent so that the liquid or other contents 30 of the bag leave an airspace 31 within the bag so as not to plug ports 17A, 17B and 14 when the bag is lying flat on bottom wall 12.

Referring to FIG. 3, there is shown use of bag 10 subsequent to reconstitution of its contents (preferably lyophilized blood or red blood cells), whereby the liquid contents may be drained through either of the ports 17A or 17B. Bag 10 is suspended from hook 41 through one of the orifices 19 in tab 18.

In the preferred method of using bag 10, after inserting the reinforcing inserts, including the reinforcing and thermoconducting copper plate along bottom wall 12, the plug 16 from the major port 14 is unsealed and adapted with a sterile filter (not shown in FIG. 1). One of the ports (17B) is then unsealed and affixed with a conduit for filling the bag with its liquid contents to be lyophilized. Hereinafter the contents will be described as being blood.

The bag 10 is filled to a level below ports 17A and 17B and the port 17B is resealed or the conduit thereto is closed by an appropriate valve or other means.

The entire bag 10 is then placed within a lyophilizer, the contents are frozen and lyophilized. Cooling of the contents of the bag is assisted through the copper plate (not shown) on the exterior of the bottom of the bag. The vapor is removed through port 14 (unsealed), plug 16 and a sterile filter (not shown). The bag is prevented from collapsing by the reinforcing inserts 21 (and 24) and the copper plate. Upon completion of lyophilization, the vacuum in the lyophilizer is released by venting with sterile, dry inert gas such as nitrogen. The vacuum inside the blood bag is thereby replaced with inert gas via port 14 (unsealed), plug 16 and the attached sterile filter (not shown). The bag is then removed from the lyophilizer and conduit 15 is sealed and may be cut to remove excess tubing, plug 16 and the sterile filter. This creates a fully sealed sterile environment for storage of the dry product in the closed bag under a dry inert gas. The copper plate is then removed from the exterior of bottom wall 12. If desired, the inserts 24 and 21 may also be removed. The bag and its lyophilized contents may then be stored under a range of temperatures, from −80° C. to +25° C. (room temperature), and even in excess of normal room temperatures.

When the contents of the bag are to be reconstituted, port 17B and (17A, if needed) may be unsealed and used for entry and withdrawal for appropriate reconstitution fluids. To use the reconstituted fluids in the bag, the bag is suspended, preferably as shown in FIG. 3, and its contents are withdrawn through one or more of the ports 17A or 17B.

It should be apparent in FIGS. 1 and 3 that while only two side ports 17A and 17B are shown, the bag may be manufactured with as many ports as desired.

A particular advantage of the bag according to the present invention is that it conserves space before use since it may then be collapsed to virtually a flat piece before the reinforcing inserts are inserted. The bag may then be filled, used in a lyophilizer, stored, used for reconstitution, and then drained of its contents, without ever transferring the desirable contents from the bag.

It will also be realized that means other than by tab 18 and orifices 19 may be utilized to suspend the bag, such as by loops, hooks, etc.

It will also be realized that after lyophilization is complete the bag is sealed to create a self-contained environment suitable for storage of the dried contents. Removal of excess tubing, plugs, and appended sterile filter after sealing of the bag, as well as removal of all copper plates and semi-rigid wall supports will also serve to reduce the final weight of the sealed bag and its contents. It will be realized that conservation of weight per sealed bag offers important storage and transport advantages.

We claim:

1. A flexible plastic bag comprising an upper wall and lower wall, said walls sealed at their edges to a peripheral side wall to thereby define the inner volume of said bag;

a major port in said upper wall approximately centrally located in said upper wall, said major port adapted with a sealable conduit;

at least one side port in said side wall, said side port adapted with sealing means and said side port located proximate to the upper edge of said side wall;

securing means on said peripheral side wall adapted to receive removable rigid or semirigid reinforcing members to restrain said side wall from collapse when said reinforcing members are secured to said side wall;

securing means in said upper wall adapted to receive removable rigid or semi-rigid reinforcing members to restrain said upper wall from collapse when said reinforcing members are secured to said upper wall;

securing means on said lower wall adapted to receive removable semi-rigid or rigid lower reinforcing means, wherein said lower reinforcing means comprises a thermoducting material to facilitate conduction of heat to or from the contents of said bag through said lower wall; and attachment means for suspending said bag in a position whereby at least one of said side ports is at a location for withdrawal of any fluid contents from said bag.

2. A bag according to claim 1 wherein said sealable conduit is adapted with a sterile filter.

3. A bag according to claim 1 comprising at least two of said side ports.

4. A bag according to claim 1 wherein said securing means on said peripheral side wall and on said upper wall comprise loops adapted to receive said reinforcing members in the form of strips.

5. A bag according to claim 1 wherein said securing means on said lower wall comprises a flexible plastic sheet sealed on three edges to said lower wall and to said peripheral wall, thereby forming an exterior open-ended pocket with said lower wall.

6. A lyophilization plastic bag comprising a flexible plastic bag according to claim 1, and said rigid or semi-rigid reinforcing strips retained by said loops against said upper wall and peripheral wall.

7. A lyophilization bag according to claim 6 further comprising a thermally conducting metal plate accommodated by said pocket on said lower wall.

8. A lyophilization bag according to claim 7 wherein said metal plate comprises copper.

9. A method for lyophilizing a fluid product comprising the steps of:
    (a) providing a container according to claim 1 adapted with said reinforcing members in said peripheral wall and upper wall and with said lower reinforcing members in lower wall, and with a sterile filter on said sealable conduit;
    (b) positioning said bag from step (a) in a lyophilizer whereby said lower wall is downwardly facing;
    (c) introducing said fluid product through at least one of said side ports into said bag to a level at which said major port is in communication with the vapor space within said bag not occupied by said fluid product; and resealing said port;
    (d) freezing and lyophilizing the contents of said bag whereby vapors are withdrawn from said bag through said major port, conduit and filter;
    (e) backfilling said bag with sterile dry inert gas and withdrawing said bag from said lyophilizer; and
    (f) sealing said sealable conduit.

10. A method according to claim 9 wherein said fluid product comprises blood.

11. A method according to claim 9 wherein said fluid product comprises red blood cells for transfusion.

12. A method according to claim 9 further comprising the step (g) of introducing at least one sterile reconstitution solution into said bag through at least one of said side ports to produce a rehydrated sterile solution suitable for subsequent pharmaceutical use.

13. A method according to claim 9 wherein said fluid product comprises blood components prepared from whole blood, to include serum or blood protein fractions derived from serum.

14. A method according to claim 9 wherein said fluid product comprises a protein-containing solution.

* * * * *